(12) United States Patent
Chang et al.

(10) Patent No.: US 11,795,065 B2
(45) Date of Patent: *Oct. 24, 2023

(54) IRON OXIDE MAGNETIC PARTICLES

(71) Applicant: ZTI Biosciences Co., Ltd., Daejeon (KR)

(72) Inventors: Hyungseok Chang, Seoul (KR); Sei Jin Park, Seoul (KR); Yong-Sun Park, Seoul (KR); Ji Young Ryu, Yongin-si (KR); Yoon-Sik Lee, Anyang-si (KR)

(73) Assignee: ZTI BIOSCIENCES CO., LTD., Daejeon (KR)

( * ) Notice: Subject to any disclaimer, the term of this patent is extended or adjusted under 35 U.S.C. 154(b) by 239 days.

This patent is subject to a terminal disclaimer.

(21) Appl. No.: 17/187,591

(22) Filed: Feb. 26, 2021

(65) Prior Publication Data

US 2021/0327621 A1 Oct. 21, 2021

(30) Foreign Application Priority Data

Apr. 13, 2020 (KR) .................. 10-2020-0044724
Apr. 13, 2020 (KR) .................. 10-2020-0044735

(51) Int. Cl.
| | | |
|---|---|---|
| *H01F 1/00* | (2006.01) | |
| *H01F 1/34* | (2006.01) | |
| *H01F 1/06* | (2006.01) | |
| *H01F 1/09* | (2006.01) | |
| *C01G 49/06* | (2006.01) | |
| *B82Y 5/00* | (2011.01) | |
| *B82Y 25/00* | (2011.01) | |
| *B82Y 30/00* | (2011.01) | |
| *B82Y 40/00* | (2011.01) | |

(52) U.S. Cl.
CPC ........... *C01G 49/06* (2013.01); *H01F 1/0054* (2013.01); *H01F 1/342* (2013.01); *B82Y 5/00* (2013.01); *B82Y 25/00* (2013.01); *B82Y 30/00* (2013.01); *B82Y 40/00* (2013.01); *C01P 2002/72* (2013.01); *C01P 2002/85* (2013.01); *C01P 2004/04* (2013.01); *C01P 2004/64* (2013.01); *C01P 2006/42* (2013.01)

(58) Field of Classification Search
CPC .......... H01F 1/0054; H01F 1/342; H01F 1/03; H01F 1/0315; H01F 1/06; H01F 1/061; H01F 1/063; H01F 1/09; C01G 49/04; C01G 49/06; C01G 49/08; C01P 2006/42; C01P 2002/52; A61K 41/0052

See application file for complete search history.

(56) References Cited

FOREIGN PATENT DOCUMENTS

| | | |
|---|---|---|
| JP | 2011-516279 A | 5/2011 |
| JP | 2013-534893 A | 9/2013 |
| JP | 2014-111600 A | 6/2014 |
| JP | 2014-528920 A | 10/2014 |
| JP | 2015-199726 A | 11/2015 |
| JP | 2019-536716 A | 12/2019 |
| KR | 10-2012-0013519 A | 2/2012 |
| KR | 10-2015-0092743 A | 8/2015 |
| KR | 10-2019-0010324 A | 1/2019 |

OTHER PUBLICATIONS

Liang et al., "Facile synthesis of magnetic Fe3O4@BiOl@AgI for water decontamination with visible light irradiation: Different mechanisms for different organic pollutants degradation and bacterial disinfection", Mar. 10, 2018, Water Research 137, pp. 120-129. (Year: 2018).*
Yang et al., "cRGD-functionalized, DOX-conjugated, and 64Cu-labeled superparamagnetic iron oxide nanoparticles for targeted anticancer drug deliver and PET/MR imagining", Mar. 2, 2011, Biomaterials 32, pp. 4151-4160. (Year: 2011).*
R.V. Mazurenko et al., "Synthesis, Electrical and Magnetic Properties of Composites Copper Iodide/Magnetite-Polychlorotrifluoroethylene", Physics and Chemistry of Solidstate, May 6, 2017, p. 215-221, V. 18, No. 2, Chuiko Institute of Surface Chemistry of the NAS of Ukraine, Ukraine.
Dipranjan Laha, et al., "Evaluation of copper iodide and copper phosphate nanoparticles for their potential cytotoxic effect", The Royal Society of Chemistry 2012, Mar. 14, 2012, Toxicol. Res., 2012, 1, 131-136, Department of Life Science and Biotechnology, Jadavpur University, Kolkata, India.
Fernandez-Barahona et al., "Cu-Doped Extremely Small Iron Oxide Nanoparticles with Large Longitudinal Relaxivity: One-Pot Synthesis and in Vivo Targeted Molecular Imaging", ACS Omega, 2019, vol. 4, pp. 2719-2727 (9 pages total).
Ebrahimisadr et al., "Magnetic Hyperthermia Properties of Iron Oxide Nanoparticles: The Effect of Concentration", Physica C: Superconductivity and its applications, 2018 (6 pages total).
Japanese Notice of Reasons for Refusal dated Nov. 8, 2022, in Japanese Application No. 2021-569348.

* cited by examiner

*Primary Examiner* — Matthew E. Hoban
*Assistant Examiner* — Lynne Edmondson
(74) *Attorney, Agent, or Firm* — Sughrue Mion, PLLC

(57) ABSTRACT

The present invention provides iron oxide magnetic particles including an iron oxide and $MX_n$, wherein M includes one or more selected from the group consisting of Cu, Sn, Pb, Mn, Ir, Pt, Rh, Re, Ag, Au, Pd, and Os, X includes one or more selected from the group consisting of F, Cl, Br, and I, and n is an integer of 1 to 6.

5 Claims, 6 Drawing Sheets

IRON OXIDE MAGNETIC PARTICLES

CROSS-REFERENCE TO RELATED APPLICATIONS

This application claims the priority of Korean Patent Application No. 10-2020-0044735 filed on Apr. 13, 2020 and No. 10-2020-0044724 filed on Apr. 13, 2020 in the Korean Intellectual Property Office, the disclosure of which is incorporated herein by reference.

BACKGROUND OF THE INVENTION

Field of the Invention

The present invention relates to iron oxide magnetic particles.

Description of the Related Art

Magnetic particles have been widely used in the biomedical field including, cell labeling, magnetic resonance imaging (MRI), drug delivery, and hyperthermia. Among various kinds of magnetic particles, superparamagnetic iron oxide magnetic particles have high magnetic susceptibility and superparamagnetism, and thus, have been widely studied in the biomedical field.

In addition, magnetic particles are characterized by generating heat when radiation or a magnetic field is applied thereto, and thus, may also be used as a contrast agent of a magnetic resonance imaging (MRI) device, a magnetic carrier for drug delivery in the nanomedicine field, or for magnetic or radiation-based thermotherapy, and the like.

In the imaging diagnosis field, an iron oxide, which is a superparamagnetic contrast agent, is proposed as a negative contrast agent. However, iron oxide particles have strong hydrophobic attraction, and thus, aggregate well with each other, thereby forming a cluster, or when exposed to a bioenvironment, the iron oxide particles are subjected to quick biodegradation. In addition, when the structure of iron oxide particles is not sufficiently stable, the structure itself may change, causing a change in the magnetic properties of the iron oxide particles as well, which may allow the particles to become toxic. On the other hand, iodine is proposed as a positive contrast agent, but when used in high concentration to increase the contrast effect, the iodine causes liver/kidney toxicity. Therefore, a formulation technology for increasing the content per volume of a contrast medium have been used.

Meanwhile, radiation-based or electromagnetic field-based thermotherapy has been proposed to overcome the limitations of typical cancer treatment methods (Wust et al. Lancet Oncology, 2002, 3:487-497). One of the unique properties of cancer cells is that the ability thereof to adapt to heat is significantly lower than that of normal cells. Thermotherapy is an anti-cancer therapy that selectively kills cancer cells by raising the temperature of cancer tissues and their surroundings to about 40° C. to 43° C. using the difference in thermal sensitivity between normal cells and cancer cells. When a magnetic field is applied from the outside by injecting magnetic particles around cancer cells, heat is generated from the magnetic particles, so that the cancer cells may be killed in a short period of time. Since a magnetic field is not affected by skin tissues, there is no limit to the penetration depth of the magnetic field, so that heat may be selectively applied when magnetic particles are accumulated in cancer tissues in a body. Thus, research on thermotherapy using magnetic particles has attracted a lot of attention.

Iron oxide magnetic particles are mainly used as magnetic particles for thermotherapy, as well. This is because iron oxide magnetic particles is a material having an indirect band gap in which energy as much as momentum used is converted into heat and then released. Among them, $Fe_3O_4$ (magnetite)-based or $\alpha$-Fe(ferrite)-based magnetic particles have bio-compatibility, heat-inducing ability, chemical stability, and unique magnetic properties. Due to the above properties thereof, $Fe_3O_4$ (magnetite)-based or $\alpha$-Fe (ferrite)-based magnetic particles have been subjected to active research as a magnetic heating element for thermotherapy, and have been approved for medical use by the FDA of the Unites States of America. However, among iron oxide magnetic particles, $Fe_3O_4$ particles are nano-sized, and the crystal phase thereof are easily changed to $\alpha$-$Fe_2O_3$, $\gamma$-$Fe_3O_4$, and the like depending on the conditions of the surrounding environment, and thus, have a disadvantage in that the exothermic properties and magnetic properties thereof change accordingly, resulting in the decrease in heat generation ability. As for another material, research is being conducted on Co, Ni, and Mg-based $MFe_2O_4$ (M=Co,Ni, Mg) nanoparticles. However, they also have a disadvantage in that it is difficult to apply the same in vivo due to a low exothermic temperature thereof.

PRIOR ART DOCUMENT

Non-patent literature: Wust et al. Lancet Oncology, 2002, 3:487-497

SUMMARY OF THE INVENTION

An aspect of the present invention provides iron oxide magnetic particles which may be used in various fields.

In order to solve the above problem, the present invention provides iron oxide magnetic particles including an iron oxide and $MX_n$, wherein M includes one or more selected from the group consisting of Cu, Sn, Pb, Mn, Ir, Pt, Rh, Re, Ag, Au, Pd, and Os, X includes one or more selected from the group consisting of F, Cl, Br, and I, and n is an integer of 1 to 6.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
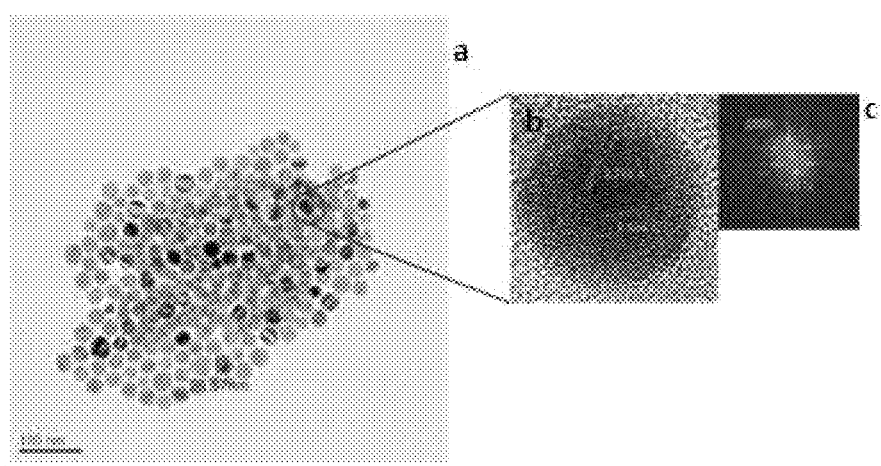
FIG. 1 illustrates the results of observing $CuI/Fe_3O_4$ particles prepared according to an embodiment of the present invention using a transmission electron microscope (a: Transmission Electron Microscope (TEM) image, b: High-Resolution Transmission Electron Microscope (HR-TEM) image, c: Fast Fourier Transform (FTT) image)
Figure 2:
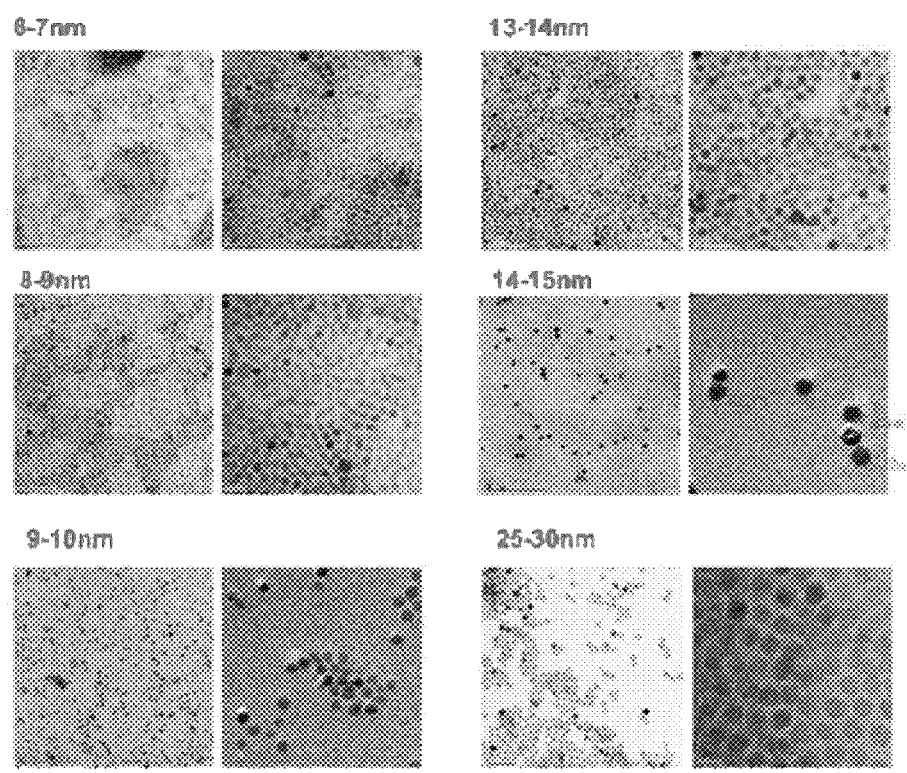
FIG. 2 illustrates the results of observing $CuI/Fe_3O_4$ particles of various sizes prepared according to an embodiment of the present invention using a transmission electron microscope.

Exemplary embodiments of the present invention will now be described in detail with reference to the accompanying drawings.

Hereinafter, various embodiments of the present invention will be described with reference to the accompanying drawings. It should be understood that the present invention is not limited to a embodiment, and includes various modifications, equivalents, and/or alternatives of embodiments of the present invention. With respect to the description of the drawings, similar reference numerals may be used for similar elements.

In this document, the phases such as "have," "may have," "include," or "may include" refer to the presence of a corresponding feature (e.g., elements such as figures, functions, operations, or parts), and does not exclude the presence of additional features.

In this document, the phrases such as "A or B," "at least one of A or/and B," or "one or more of A or/and B" may include all possible combinations of items listed together. For example, "A or B," "at least one of A and B," or "at least one of A or B" may refer to all cases including (1) at least one A, (2) at least one B, or (3) at least one A and at least on B.

The phrase "configured to (or set)" used in this document may be used, depending on the context, interchangeably with, for example, "suitable for," "having the capacity to," "designed to," "adapted to," "made to," or "capable of." The term "configured (or set)" does not necessarily mean "specifically designed to" only.

The terms used in this document are only used to describe specific embodiments, and may not be intended to limit the scope of other embodiments. Singular expressions may include plural expressions unless the context clearly indicates otherwise. Terms used herein, including technical or scientific terms, may have the same meanings as those commonly understood by those with ordinary knowledge in the technical field described in this document. Among the terms used in this document, terms defined in a general dictionary may be interpreted as having the same or similar meaning to the meaning in the context of a relevant art, and are not interpreted as having an ideal or excessively formal meaning, unless explicitly defined otherwise in this document. In some cases, even the terms defined in this document should not be interpreted to exclude embodiments of this document.

The embodiments disclosed in this document have been presented for the description and understanding of the disclosed technical content, and are not intended to limit the scope of the present invention. Therefore, the scope of this document should be construed to include all changes or various other embodiments based on the technical spirit of the present invention.

Hereinafter, preferred embodiments of the present invention will be described in detail. Prior to this, it will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

Therefore, the configurations of the embodiments described herein are merely some of preferred embodiments of the present invention, and are not intended to limit the technical idea of the present invention. Therefore, it should be understood that there may be various equivalents and modifications that may substitute the embodiments at the time of the present application.

Throughout the specification, when a portion is said to "include" any component, it means that the portion may further include other components rather than excluding the other components unless otherwise stated.

In one aspect of the present disclosure, the term "about" was used with the intention of including errors of a manufacturing process included in a specific numerical value or a slight numerical adjustment that falls within the scope of the technical idea of the present disclosure. For example, the term "about" means a range of ±10% of the value it refers to, a range of ±5% in one aspect, and a range of ±2% in another aspect.

Hereinafter, the present invention will be described in detail.

Iron oxide magnetic particles according to an embodiment of the present invention are iron oxide magnetic particles including an iron oxide and MXn, wherein M includes one or more selected from the group consisting of Cu, Sn, Pb, Mn, Ir, Pt, Rh, Re, Ag, Au, Pd, and Os, X includes one or more selected from the group consisting of F, Cl, Br, and I, and n is an integer of 1 to 6.

The term "iron oxide" refers to an oxide of iron, which The term "iron oxide" refers to an oxide of iron, which may include, but is not limited to, for example, one or more selected from the group consisting of $Fe_{13}O_{19}$, $Fe_3O_4$ (magnetite), $\gamma$-$Fe_2O_3$ (maghemite), and $\alpha$-$Fe_2O_3$ (hematite), $\beta$-$Fe_2O_3$ (beta phase), $\epsilon$-$Fe_2O_3$c (epsilon phase), FeO (Wustite), $FeO_2$ (Iron Dioxide), $Fe_4O_5$, $Fe_5O_6$, $Fe_5O_7$, $Fe_{25}O_{32}$, and a delafossite.

The term "heavy atom" includes, but is not limited to, for example, atoms heavier than B (boron), such as Mn, Co, Cu, Se, Sr, Mo, Ru, Rh, Pd, Ag, Cd, Sn, Ba, Ta, W, Re, Os, Ir, Pt, Au, Hg, Tl, and Pb.

According to an embodiment of the present invention, the M may be Cu.

In addition, the $MX_n$ may include one or more selected from the group consisting of CuF, $CuF_2$, $CuF_3$, CuCl, $CuCl_2$, CuBr, $CuBr_2$, CuI, $CuI_2$, and $CuI_3$, and preferably, the $MX_n$ may include one or more selected from the group consisting of CuF, CuCl, CuBr, and CuI.

In addition, the X may include a radioactive isotope of X or a mixture of radioactive isotopes of X. The term "radioactive isotope" refers to all compounds in which one or more atoms are replaced by an atom having the same atomic number but having atomic mass or mass number different from the atomic mass or mass number commonly found in nature. Examples of isotopes suitable to be included in the compound of the present invention are isotopes of fluorine, for example, $^{18}F$, isotopes of chlorine, for example, $^{36}Cl$, isotopes of bromine, for example, $^{75}$Br, $^{76}$Br, $^{77}$Br, and $^{82}$Br, and isotopes of iodine, for example, $^{123}$I, $^{124}$I, $^{125}$I, and $^{131}$I, alone or in combination.

According to the present invention, the meaning of $MX_n$ being included in iron oxide particles is that a physical or chemical bond is formed between the iron oxide particles and the $MX_n$. Specifically, it may be that $MX_n$ is disposed between iron oxide particles, or may be that an iron oxide and $MX_n$ are bonded through hydrogen bonding, or it may include that the $MX_n$ is formed by introducing a typical coating method on the surface of an iron oxide core, or formed by introducing a doping method, such as a diffusion process or ion injection process, or that an iron oxide crystal nucleus is formed inside the $MX_n$ to form a shell structure.

Particles including $MX_n$ in iron oxide particles have magnetism, and may amplify the contrast effect of an iron oxide under relatively low alternating magnetic field intensity and/or a low frequency magnetic field or various radiation conditions.

In addition, the iron oxide magnetic particles of the present invention have very stable bonds between iron oxide particles and a heavy atom-halogen compound and between heavy atom-halogen, so that there is little risk of side effects which may be caused by each constituent component, that is, an iron oxide, a heavy atom, and a halogen element.

In one specific example, the iron oxide magnetic particles may be configured such that at least a portion of the surface of the iron oxide Magnetic particles is coated with a hydrophilic ligand or a charged ligand or a polymer. The hydrophilic ligand may be introduced to increase the solubility of the iron oxide magnetic particles according to one specific example in water and increase stabilization, or to enhance targeting or penetration for specific cells, such as cancer cells. Such a hydrophilic ligand may preferably have biocompatibility, and may include, for example, one or more selected from the group consisting of polyethylene glycol, polyethylene amine, polyethylene imine, polyacrylic acid, polymaleic anhydride, polyvinyl alcohol, polyvinylpyrrolidone, polyvinyl amine, polyacrylamide, polyethylene glycol, phosphate-polyethylene glycol, polybutylene terephthalate, polylactic acid, polytrimethylene carbonate, polydioxanone, polypropylene oxide, polyhydroxyethyl methacrylate, starch, dextran derivative, sulfonic acid, amino acid, sulfonic acid peptide, silica, and polypeptide, but is not limited thereto. If necessary, when targeting cancer cells, as the hydrophilic ligand, a peptide or protein including folic acid, transferrin, or RGD may be used, and hyaluronidase or collagenase may be used to enhance penetration into cells, but the hydrophilic ligand is not limited thereto.

An iron oxide included in the iron oxide magnetic particles of the present invention may be derived from a composite of iron and one or more compounds selected from the group consisting of an aliphatic hydrocarbonate having 4 to 25 carbon atoms and an amine compound.

Examples of the aliphatic hydrocarbonate having 4 to 25 carbon atoms may include one or more selected from the group consisting of butyrate, valerate, caproate, enanthate, caprylic acid, pelargonate, caprate, laurate, myristate, pentadecylate, acetate, palmitate, palmitoleate, margarate, stearate, oleate, vaccenate, linoleate, (9,12,15)-linoleate, (6,9,12)-linoleate, eleostearate, tuberculasterate, larchidate, arachidonate, behenate, lignocerate, nervonate, serotate, montanate, melisate, and a peptide salt including one or more amino acids. A compound thereof may be used alone or in the form of two or more mixed acid salts.

A metal component of the aliphatic hydrocarbonate having 4 to 25 carbon atoms may include one or more selected from the group consisting of calcium, sodium, potassium, and magnesium.

Examples of the amine compound may include one or more selected from the group consisting of methylamine, ethylamine, propylamine, isopropylamine, butylamine, amylamine, hexylamine, octylamine, 2-ethylhexylamine, nonylamine, decylamine, laurylamine, pentadecylamine, cetylamine, stearylamine, and cyclohexylamine, dimethylamine, diethylamine, dipropylamine, diisopropylamine, dibutylamine, diamylamine, dioctylamine, di(2-ethylhexyl)amine, didecylamine, dilaurylamine, dicetylamine, distearylamine, methylstearylamine, ethylstearylamine, and butylstearylamine, triethylamine, triamylamine, trihexylamine and trioctylamine, triallylamine and oleylamine, laurylaniline, stearylaniline, triphenylamine, N,N-dimethylaniline and dimethylbenzylaniline, monoethanolamine, diethanolamine, triethanolamine, dimethylaminoethanol, diethylenetriamine, triethylene tetramine, tetraethylenepentaamine, benzylamine, diethylaminopropylamine, xylylenediamine, ethylenediamine, hexamethylenediamine, dodecamethylenediamine, dimethylethylenediamine, triethylenediamine, guanidine, diphenylguanidine, N,N,N',N'-tetramethyl-1,3-butanediamine, N,N,N',N'-tetramethylethylenediamine, 2,4,6-tris(dimethylaminomethyl)phenol, morpholine, N-methylmorpholine, 2-ethyl-4-methylimidazole and 1,8-diazabicyclo (5,4,0)undecene-7 (DBU).

The content of $MX_n$ in iron oxide magnetic particles may be calculated during a manufacturing process of iron oxide magnetic particles according to an embodiment of the present invention. A compound selected from the group consisting of an aliphatic hydrocarbonate having 4 to 25 carbon atoms and an amine compound forms a composite with iron, and then the composite forms an iron oxide through a series of processes. The content of $MX_n$ introduced when bonding the $MX_n$ to the formed iron oxide may be based on a total of 100 mol % of the composite.

Specifically, iron oxide magnetic particles are prepared by including the $MX_n$ in an amount of about 1 to 13 mol %, preferably about 1 to 8 mol %, more preferably about 3 to 6 mol % based on 100 mol % of the composite of iron and one or more compounds selected from the group consisting of an aliphatic hydrocarbonate having 4 to 25 carbon atoms and an amine compound.

Iron oxide magnetic particles finally prepared under the above conditions may include $MX_n$ in a weight ratio of 1:0.005 to 0.8, preferably 1:0.008 to 0.08 based on an iron oxide included in the iron oxide magnetic particles (The above ratio is determined based on the results of Inductively Coupled Plasma (ICP) Mass Spectroscopy, which is metal content analysis equipment). As $MX_n$ is included in iron oxide magnetic particles within the above range, excellent specific loss power may be ensured, and a high temperature change may be ensured under an external alternating magnetic field or when radiation is irradiated.

The iron oxide magnetic particles may have an average particle diameter (d50) of 0.1 nm to 1 μm. When the iron oxide magnetic particles have an average particle diameter (d50) of 0.1 nm to 1 μm, the particles may be used as an element of a contrast agent, an anticancer drug, a thermotherapy agent, or a radiation therapy agent. When the size of the iron oxide magnetic particles exceeds 100 nm, the particles may be applied to various in vitro medical fields.

In one specific example, the average particle diameter (d50) of the iron oxide magnetic particles may be adjusted according to an administration method, an administration position, and an organ to be diagnosed. For example, when the particles have a size of 0.1 to 100 nm, if the average particle diameter (d50) thereof is about 15 nm or less, intravenous injection may be preferable, and if the average particle diameter (d50) thereof is greater than 15 nm, intralesional and intratumor injections may be preferable.

The iron oxide magnetic particles as described above may ensure high specific loss power while having high reactivity to a stimulus introduced from the outside, such as radiation, magnetic fields, and radio waves, and thus, may be effectively used for thermotherapy to be described later.

Presumably, in the case of a heavy atom-halogen compound such as $MX_n$, the dielectric constant and capacitance vary depending on the type of the heavy atom and the type of halogen (as an atomic shell grows from F to I on the periodic table, there is a difference in dielectric constant/electron capacitance), so that by bonding the compound with an iron oxide, which is a magnetic body, it is possible to increase magnetic strength, and by increasing the size or total amount of electromagnetic field energy that the compound may absorb, it is possible to increase the amount of thermal energy emitted by final iron oxide-based magnetic particles. This may improve or increase the high thermal energy emission (conversion) efficiency (ILP: Intrinsic loss power) compared to typical iron oxide-based magnetic particles, not only in a typical high-frequency (200 kHz or more) range, but also in an electromagnetic field energy environment of low-frequency and medium-frequency (50 Hz to 200 kHz) bands, which are relatively low.

In addition, a contrast agent including the iron oxide magnetic particles may be applied to various imaging diagnosis devices, and sufficient images may be obtained by administering a small dose.

Furthermore, since the structural stability is high due to the bond formed between an iron oxide and a heavy atom-halogen compound, there is no risk of side effects which may be caused by each constituent component, and the toxicity is low, so that safe application to a human body is possible.

The iron oxide magnetic particles according to an embodiment of the present invention may be used as a contrast agent, or may be used for radiation therapy or thermotherapy to kill cancer cells.

According to an embodiment of the present invention, the iron oxide magnetic particles may be included in a composition for bio-imaging. The iron oxide magnetic particles according to the present invention have magnetism, and thus, may be usefully used in a diagnostic method using magnetic properties.

According to an embodiment of the present invention, the present invention provides a method for diagnosing cancer, the method including the steps of (a) administering a composition including the iron oxide magnetic particles to a cancer suspect patient, and (b) detecting the presence of the iron oxide magnetic particles in the patient by using a magnetic resonance device. When the iron oxide magnetic particles according to the present invention are administered, for example, it is possible to confirm a contrast effect in which the contrast between a lesion and a normal tissue is clearly enhanced and visualized in MRI T1- and T2-weighed images.

When the iron oxide magnetic particles of the present invention are administered, it is possible to diagnose cancer without separately administering an additional contrast agent, so that cancer diagnosis and treatment may be simultaneously performed using the iron oxide magnetic particles of the present invention.

If the iron oxide magnetic particles of the present invention are bonded with a cancer cell targeting material or a penetration enhancing material, it is possible to perform thermal diagnosis and treatment more efficiently under an external alternating magnetic field or radiation irradiation.

In one specific example, when the iron oxide magnetic particles of the present invention are included in a contrast agent composition, the iron oxide magnetic particles of the present invention may be included in an amount of 0.1 to 15 wt %, 1 to 15 wt %, 1 to 10 wt %, 3 to 10 wt %, or 4 to 8 wt % based on 100 wt % of the contrast agent composition.

When iron oxide magnetic particles are included within the range described above, the iron oxide magnetic particles are discharged to the outside of a body without being accumulated in the body, and thus, may significantly reduce the toxicity of a contrast agent.

In one specific embodiment, the contrast agent may exhibit a contrast effect in a magnetic field having a frequency of 1 kHz to 1 MHz or an intensity of 20 Oe (1.6 kA/m) to 200 Oe (16 kA/m). An alternating magnetic field which is irradiated after the contrast agent is administered to an individual may have a frequency of 1 kHz to 1 MHz, or a frequency of 30 kHz to 120 kHz. In general, in order to convert the spin state from singlet to triplet, an alternating magnetic field of 1 MHz or greater should be applied. However, in the case of the present invention, triplet interconversion is possible even under an alternating magnetic field of tens to hundreds of kHz. In addition, an alternating magnetic field may have a magnetic field intensity of 20 Oe (1.6 kA/m) to 200 Oe (16.0 kA/m), 80 Oe (6.4 kA/m) to 160 Oe (12.7 kA/m), or 140 Oe (11.1 kA/m). A contrast agent according to one specific example is useful in that it may be used in an alternating magnetic field having a low magnetic field intensity and/or frequency, which is relatively harmless to a human body, unlike a typical high-energy method.

A contrast agent including the iron oxide magnetic particles of the present invention is characterized by not being limited to a device which may be applied for image diagnosis. The contrast agent including the iron oxide magnetic particles of the present invention has both a negative contrast agent component and a positive contrast agent component, and thus, has a high degree of contrast, thereby exhibiting an excellent contrast effect. Particularly, the contrast agent including the iron oxide magnetic particles of the present invention exhibits a radiation absorption hounsfield unit (HU) value and a CT contrast effect higher than those of a conventional iodine-based (Iohexol or Iopamidol) contrast agent or gold nano CT contrast agents. It is reported that a typical iodine-based contrast agent has a value of 3000 HU based on 647 mg/ml (which is 4.6 HU based on 1 mg), and gold nanoparticles have a value of about 5 to 50 HU based on 1 mg. On the other hand, the contrast agent including the iron oxide magnetic particles of the present invention exhibits a value of about 50 to 100 HU based on 1 mg.

The present invention has an effect as a CT contrast agent, and may also be used as a contrast agent for X-ray images, Magnetic Resonance Imaging (MRI), US, optical images, Single Photon Emission Computed Tomography (SPECT), Positron Emission Tomography (PET), Magnetic Particle Imaging (MPI), flat images, and rigid, flexible, or capsule endoscopy, and the like.

That one type of contrast agent may be used in various devices may be very useful when a complex test is required. For example, when a CT scan and an MRI scan are to be conducted within a short period of time, if a CT contrast agent 1 and an MRI contrast agent 2 are separately introduced in a body, allowing contrast agents different from each other to be mixed in the body, test result may not be accurate, and when an individual is administered with a different contrast agent for each test, the probability of causing toxicity increases. However, the contrast agent including the iron oxide magnetic particles of the present invention may be used in various devices without limitation, and thus, such inconvenience may be reduced.

Another aspect provides a composition for diagnosing a cancer, the composition including a contrast agent containing the iron oxide magnetic particles according to one specific example.

The cancer may be stomach cancer, lung cancer, melanoma, uterine cancer, breast cancer, ovarian cancer, liver cancer, biliary tract cancer, gallbladder cancer, bronchial cancer, nasopharyngeal cancer, laryngeal cancer, pancreatic cancer, bladder cancer, colon cancer, rectal cancer, colorectal cancer, cervical cancer, brain cancer, prostate cancer, bone cancer, skin cancer, blood cancer, kidney cancer, prostate cancer, thyroid cancer, parathyroid cancer, or ureteral cancer.

The composition for diagnosing a cancer may be administered to an individual in an oral or parenteral manner, and may include a pharmaceutically acceptable carrier to be suitable for each administration. Suitable pharmaceutically acceptable carriers and medicines are described in detail in a Remington's book (Remington's Pharmaceutical Sciences 19th ed., 1995).

When the composition for diagnosing a cancer is administered in an oral manner, it may be administered as a solid medicine such as tablets, capsules, pills, or granules, or as a liquid medicine such as solutions and suspensions.

When the composition for diagnosing a cancer is administered in a parenteral manner, it may be administered by intravenous injection, subcutaneous injection, intramuscular injection, intraperitoneal injection, intralesional injection, intratumoral injection, and the like.

When the composition for diagnosing a cancer is administered orally or parenterally as a liquid, it may be prepared as an aqueous solution or a suspension using a commonly known solvent such as isotonic sodium chloride solution, Hank's solution, or Ringer's solution.

In one specific example, the composition for diagnosing a cancer may be for treating a cancer at the same time.

As described above, the contrast agent including the iron oxide magnetic particles of the present invention may skill cancer cells with thermotherapy. The term "thermotherapy" means killing lesion cells as well as cancer cells by exposing body tissues to a temperature higher than a normal body temperature, or allowing such cells to have higher sensitivity to radiation therapy or anticancer drugs. Cancer thermotherapy includes whole body thermotherapy, which increases a cancer treatment effect in combination with radiation therapy/drug therapy, and loco-regional thermotherapy, which kills cancer cells by injecting iron oxide magnetic particles into a targeted solid cancer and then applying an external alternating magnetic field thereto.

As described above, a thermotherapy method has an advantage in that cancer cells may be selectively killed, thereby lowering side effects. However, a thermotherapy technology based on typical magnetic particles has a problem in that the caloric value of the particles themselves caused by an external alternating magnetic field is low and the persistence thereof is limited, so that it has been pointed out that there is a limit in thermotherapy. Typically, in order to solve the above problem, the following two methods have been used:

(a) a method of increasing the intensity or frequency of an external alternating magnetic field in order to increase the exothermic phenomenon of particles, or (b) a method of increasing the concentration of particles to be injected in vivo.

However, (a) the method of increasing the intensity or frequency of an external alternating magnetic field may cause red spots to appear around the skin and slight burns, wounds, inflammation, necrosis, and the like to appear in fatty areas, and may also damage not only cancer tissues, but also normal tissue cells, thereby lowering immunity. In addition, the method is prohibited for use in pregnant women, patients with severe inflammation, patients with cardiac pacemaker vegetation, and patients with severe hydrothorax and hydrops abdominis because side effects due to human harmfulness are unavoidable. As an alternative, (b) the method of increasing the concentration of particles to be injected in vivo increases the probability of accumulating particles in a body, and may cause a toxicity problem due to the chemical composition of the surface of the particles.

However, due to the effect of internal quantum efficiency amplification within an iron oxide caused by the difference in dielectric constant or electron capacitance due to a bonded halogen group, the iron oxide magnetic particles according to the present invention bring the result of efficient heat generation when used in thermotherapy using an external alternating magnetic fields or radiation equipment. Accordingly, the concentration of particles to be injected in vivo may be significantly lowered compared to typical iron oxide particles, and thus, problems of bio-accumulation and toxicity may be greatly prevented. In conclusion, the present invention may significantly overcome the disadvantages of the prior art which has been limited in use due to a low calorific value, despite the advantages of bio-compatibility, chemical stability, magnetic properties of iron oxide magnetic particles.

Hereinafter, Examples and the like will be described in detail to facilitate understanding of the present invention. However, Examples according to the present invention may be modified into other various forms, and the scope of the present invention should not be construed as being limited to Examples described below. Examples of the present invention are provided to more fully describe the present invention to those skilled in the art.

EXAMPLES

Example 1: Synthesis of CuI-Doped Iron Oxide Magnetic Particles

As an example of the iron oxide magnetic particles described herein, iron oxide magnetic particles having a composition of a CuI doping amount of 6 mol % were synthesized by the following method.

(a) Synthesis of Iron-Oleic Acid Composite $FeCl_3 \cdot 6H_2O$ (30 mmol) and sodium oleate (28 mmol) were mixed with 200 ml of hexane, 100 ml of ethanol, and 100 ml of deionized water, and reacted while being vigorously stirred at 110° C. for 6 hours. The reaction solution was cooled at room temperature, and then a transparent lower layer thereof was removed using a separatory funnel. 100 ml of water was mixed with a brown upper organic layer and shaken, and then a lower water layer was removed again. The above was repeated for three times. The remaining brown organic layer was transferred to a beaker and heated at 110° C. for 4 hours to allow hexane to evaporate.

(b) Synthesis of CuI-Doped Iron Oxide Magnetic Particles 4.5 g (5 mmol) of the iron-oleic acid composite, 1.7 g (6 mmol) of oleic acid, and 0.05 g (0.3 mmol) of CuI were mixed with 7 ml of 1-eicocene and 13 ml of dibenzyl ether. The mixture was placed in a round bottom flask, and gas and moisture were removed at 90° C. for about 30 minutes in a vacuum state. Nitrogen was injected thereto, and the temperature was raised to 200° C. Thereafter, the temperature of the mixture was raised to 310° C. at a rate of 3.3° C./min, and then the mixture was reacted for 60 minutes. The reaction solution was cooled, and then transferred to a 50 ml conical tube. 30 ml of ethanol and hexane were injected in a 1:1 ratio, followed by centrifugation to precipitate particles. The precipitated particles were washed with 10 ml of hexane and 5 ml of ethanol, and then an obtained precipitate was dispersed in toluene or hexane. Here, the dibenzyl ether is decomposed into benzyl aldehyde and toluene at a temperature of 150° C. or higher, and by radicals generated from the aldehyde, participates in crystal formation by helping the formation of a hydrogen bond between Iron oxo (—Fe—O—Fe—) and a heavy atom-halogen compound (CuI).

The size of particles prepared in Example 1 was about 6 to 7 nm. By adjusting the mixing amount of oleic acid to 1.84 g (6.5 mmol), 1.98 g (7 mmol), 2.12 g (7.5 mmol), and 2.26 g (8 mmol) in Step (a), particles having a size of about 8 to 9 nm, about 9 to 10 nm, about 13 to 14 nm, and about 14 to 15 nm were respectively obtained. In order to prepare particles having a size of about 20 to 30 nm, the content of oleic acid was adjusted to 2.82 g (10 mmol), and furthermore, the amount of 1-eicocene and the amount of dibenzyl ether were all adjusted to 10 ml in Step (b), and the temperature was raised to 330° C. at a rate of 3.3° C./min to perform a reaction thereon for 60 minutes.

The amount of CuI used in Example 1 was 0.05 g (0.3 mmol), and the CuI doping amount was about 6% based on the iron-oleic acid composite (5 mmol). By adjusting the input amount of CuI to 0.0057 g (0.03 mmol), 0.019 g (0.1 mmol), and 0.124 g (0.65 mmol), iron oxide magnetic particles having a CuI doping amount of about 1%, 3%, and 13% respectively were obtained.

Example 2: Preparation Particle Magnetic Particles Coated with Hydrophilic Ligand (Polyacrylic Acid)

2 g of polyacrilic acid and 40 ml of tetraethylene glycol were heated at 110° C., and then 150 mg of iron oxide magnetic particles dispersed in 5 ml of hexane was injected thereto with a syringe. The mixture was stirred and reacted at 280° C. for 8 hours. The reaction solution was cooled, and then 20 ml HCl of 0.01 M was added thereto to collect particles attracted to a magnet. After repeating the above twice, a precipitate was obtained using ethanol and was finally dispersed in water.

Example 3: Analysis of Temperature Change According to the Doping Amount of Heavy Atom-Halogen Compound Under External Alternating Magnetic Field A system for heating by inducing an alternating magnetic field consists of four main subsystems; (a) A variable frequency and amplitude sine wave function generator (20 MHz Vp-p, TG2000, Aim TTi, USA)), (b) A power amplifier (1200 Watt DC Power Supply, QPX1200SP, Aim TTi, USA), (c) An induction coil (rotation number: 17, diameter: 50 mm, height: 180 mm) and a magnetic field generator (Magnetherm RC, nanoTherics, UK), and (d) A temperature change thermocouple (OSENSA, Canada).

Figure 3:
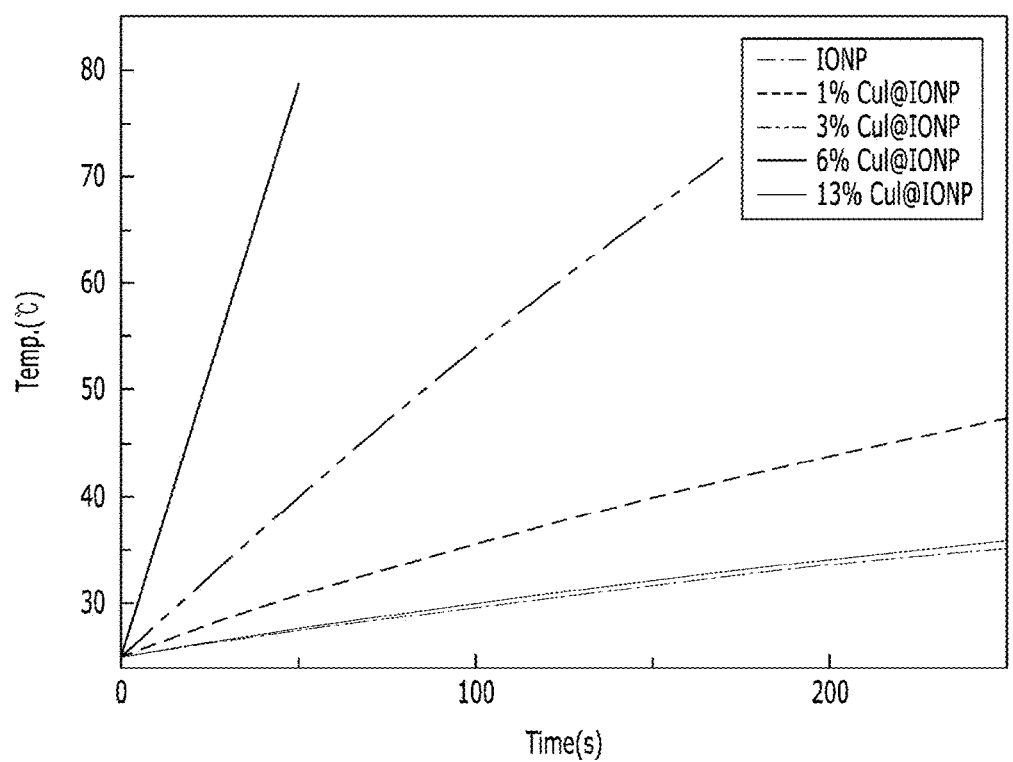
FIG. 3 is a graph showing changes in temperature over time after applying an external alternating magnetic field to $CuI/Fe_3O_4$ particles prepared by varying the CuI doping amount according to an embodiment of the present invention.

Iron oxide magnetic particles doped with CuI were prepared as described above. The iron oxide magnetic particles were diluted to a concentration of 2 mg/ml in deionized water, and then an alternating magnetic field was applied thereto to measure the temperature change using a thermocouple (OSENSA, Canada). As a result, it was confirmed that the temperature was significantly increased when CuI-doped iron oxide magnetic particles induced an alternating magnetic field (FIG. 3) compared to a control group of undoped iron oxide nanoparticles (IONP). In the order of the doping amount of CuI of 6 mol %, 3 mol %, 1 mol %, and 13 mol % based on the iron-oleic acid composite, the self-induced heating ability was more excellent.

Example 4: Measurement of Specific Loss Power (SLP)

The calorific value of iron oxide magnetic particles varies depending on the physical and chemical properties, and the intensity and frequency of an external alternating magnetic field, most research results represent the heating ability of particles as SLP and ILP. SLP is electromagnetic force lost per mass unit and is represented by W (watts) per kg. Since the conditions of f (frequency) and H (magnetic field intensity) may be different for each experiment, it is possible to compare thermotherapy effects between particles by converting an SLP value to an ILP value using the equation $[ILP=SLP/(f \cdot H^2)]$.

SLP was measured by using an alternating magnetic field generator (Magnetherm RC, Nanotherics) of a series resonance circuit controlled by a pickup coil and an oscilloscope. The measurement was performed under the thermal insulation condition of f=108.7 kHz and H=11.4 kA/m, and the temperature was measured using an optical fiber IR probe.

Figure 4:
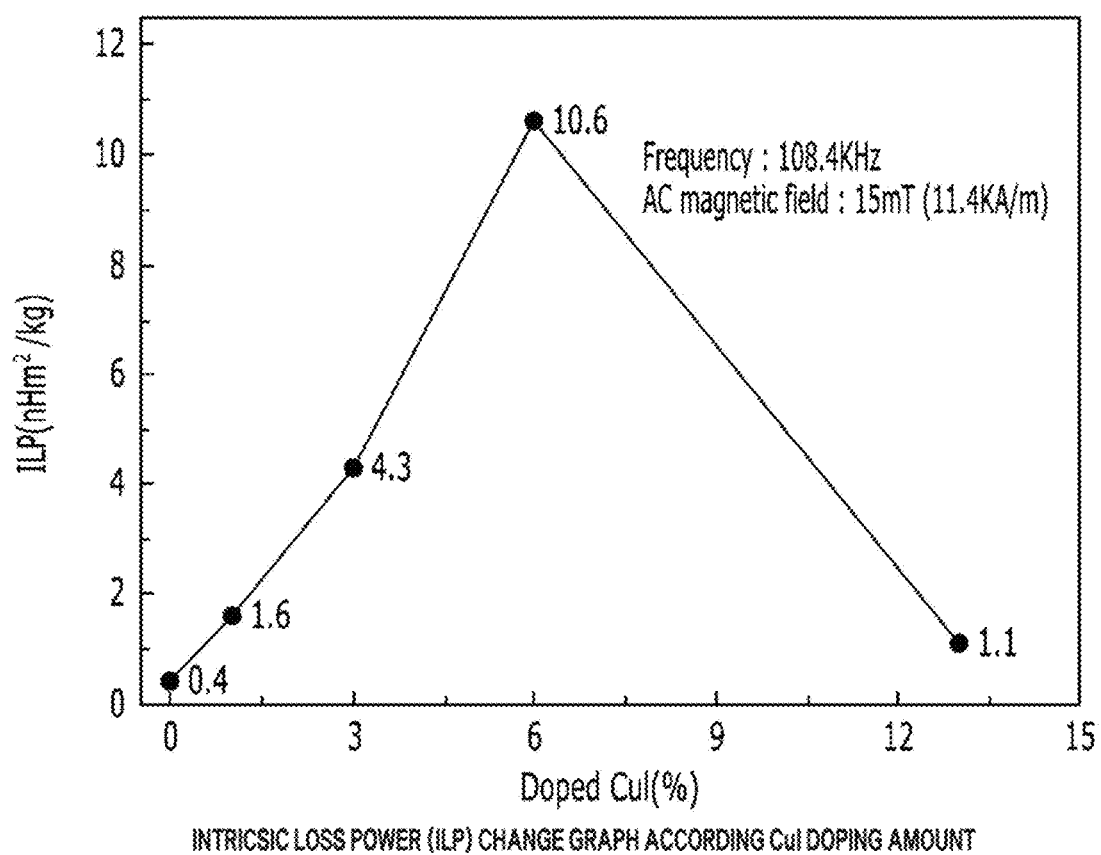
FIG. 4 is a graph showing ILP values after applying an external alternating magnetic field to CuI/Fe3O4 particles prepared by varying the CuI doping amount according to an embodiment of the present invention.
Figure 5:
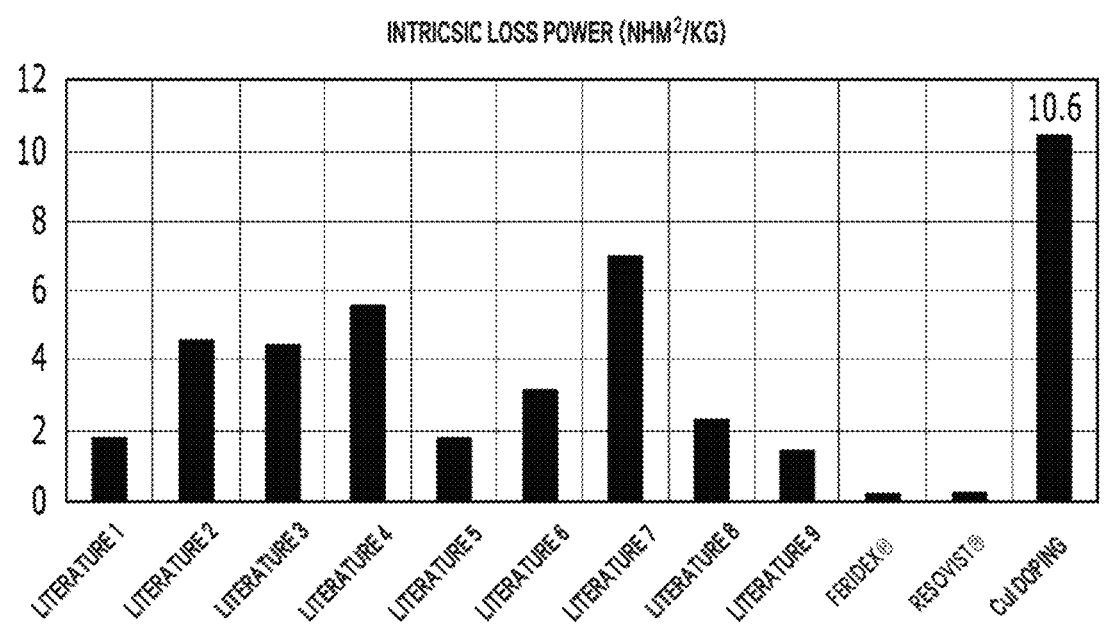
FIG. 5 is a graph comparing ILP values between particles according to an embodiment of the present invention and representative materials known in the art.

Iron oxide magnetic particles coated with polyacrilic acid were prepared as described above. SLP was measured by adjusting the concentration of the iron oxide magnetic particles to 20 mg/ml. As a result, it was confirmed that CuI-doped iron oxide magnetic particles generated high ILP under an alternating magnetic field compared to a control group of undoped iron oxide magnetic particles (FIG. 4). In the order of the doping amount of CuI of 6 mol %, 3 mol %, 1 mol %, and 13 mol % based on the iron-oleic acid composite, the self-induced heating ability was more excellent.

ILP values of representative materials known in the art and the ILP value of Example 1 of the present invention are shown in Table 1. According to Table 1, it can be confirmed that the ILP value of the iron oxide magnetic particles according to an embodiment of the present invention is increased by about 50% to 6600% compared to those of the particles known in the art.

TABLE 1

| Sample name | ILP value |
| --- | --- |
| Literature 1 | 1.75 |
| Literature 2 | 4.52 |
| Literature 3 | 4.48 |
| Literature 4 | 5.6 |
| Literature 5 | 1.84 |
| Literature 6 | 3.23 |
| Literature 7 | 7.04 |
| Literature 8 | 2.33 |
| Literature 9 | 1.47 |
| Feridex ® | 0.16 |
| Resovist ® | 0.21 |
| Example 1 | 10.6 |

[Sample Source for Comparison]

TABLE 2

| Sample | Literature title |
| --- | --- |
| Literature 1 | [Lv, Y.; Yang, Y.; Fang, J.; Zhang, H.; Peng, E.; Liu, X.; Xiao, W.; Ding, J. Size Dependent Magnetic Hyperthermia of Octahedral Fe3o4 Nanoparticles. RSC Adv. 2015, 5, 76764-76771.] |
| Literature 2 | [Liu, X. L.; Yang, Y.; Ng, C. T.; Zhao, L. Y.; Zhang, Y.; Bay, B. H.; Fan, H. M.; Ding, J. Magnetic Vortex Nanorings: A New Class of Hyperthermia Agent for Highly Efficient in Vivo Regression of Tumors. Adv. Mater. 2015, 27, 1939-1944.] |
| Literature 3 | [Yang, Y.; Liu, X.; Lv, Y.; Herng, T. S.; Xu, X.; Xia, W.; Zhang, T.; Fang, J.; Xiao, W.; Ding, J. Orientation Mediated Enhancement on Magnetic Hyperthermia of Fe3o4nanodisc. Adv. Funct. Mater. 2015, 25, 812-820.] |
| Literature 4 | [Martinez-Boubeta, C.; Simeonidis, K.; Makridis, A.; Angelakeris, M.; Iglesias, O.; Guardia, P.; Cabot, A.; Yedra, L.; Estrade, S.; Peiro, F.; Saghi, Z.; Midgley, P. A.; Conde-Leboran, I.; Serantes, D.; Baldomir, D. Learning from Nature to Improve the Heat Generation of Iron-Oxide Nanoparticles for Magnetic Hyperthermia Applications. Sci Rep. 2013, 3, 1652.] |
| Literature 5 | [Peng, E.; Choo, E. S.; Chandrasekharan, P.; Yang, C. T.; Ding, J.; Chuang, K. H.; Xue, J. M. Synthesis of Manganese Ferrite/Graphene Oxide Nanocomposites for Biomedical Applications. Small. 2012, 8, 3620-3630.] |
| Literature 6 | [Lee, J.-H.; Jang, J.-t.; Choi, J.-s.; Moon, S. H.; Noh, S.-h.; Kim, J.-w.; Kim, J.-G.; Kim, I.-S.; Park, K. I.; Cheon, J. Exchange-Coupled Magnetic Nanoparticles for Efficient Heat Induction. Nat. Nanotechnol. 2011, 6, 418-422.] |
| Literature 7 | [Muela, A.; Muoz, D.; Martin-Rodriguez, R.; Orue, I.; Garaio, E.; Abad Diaz de Cerio, A.; Alonso, J.; Garcia, J..; Fdez-Gubieda, M. L. Optimal Parameters for Hyperthermia Treatment Using Biomineralized Magnetite Nanoparticles: Theoretical and Experimental Approach. J. Phys. Chem. C. 2016, 120, 24437-24448.] |
| Literature 8 | [Alphandry, E.; Chebbi, I.; Guyot, F.; Durand-Dubief, M. Use of Bacterial Magnetosomes in the Magnetic Hyperthermia Treatment of Tumours: A Review. Int. J. Hyperthermia. 2013, 29, 801-809.] |
| Literature 9 | [Niculaes, D.; Lak, A.; Anyfantis, G. C.; Marras, S.; Laslett, O.; Avugadda, S. K.; Cassani, M.; Serantes, D.; Hovorka, O.; Chantrell, R.; Pellegrino, T. Asymmetric Assembling of Iron Oxide Nanocubes for Improving Magnetic Hyperthermia Performance. ACS Nano. 2017, 11, 12121-12133.] |

Example 5: Experiment to Confirm Cancer Treatment Effect In Vivo

Figure 6:
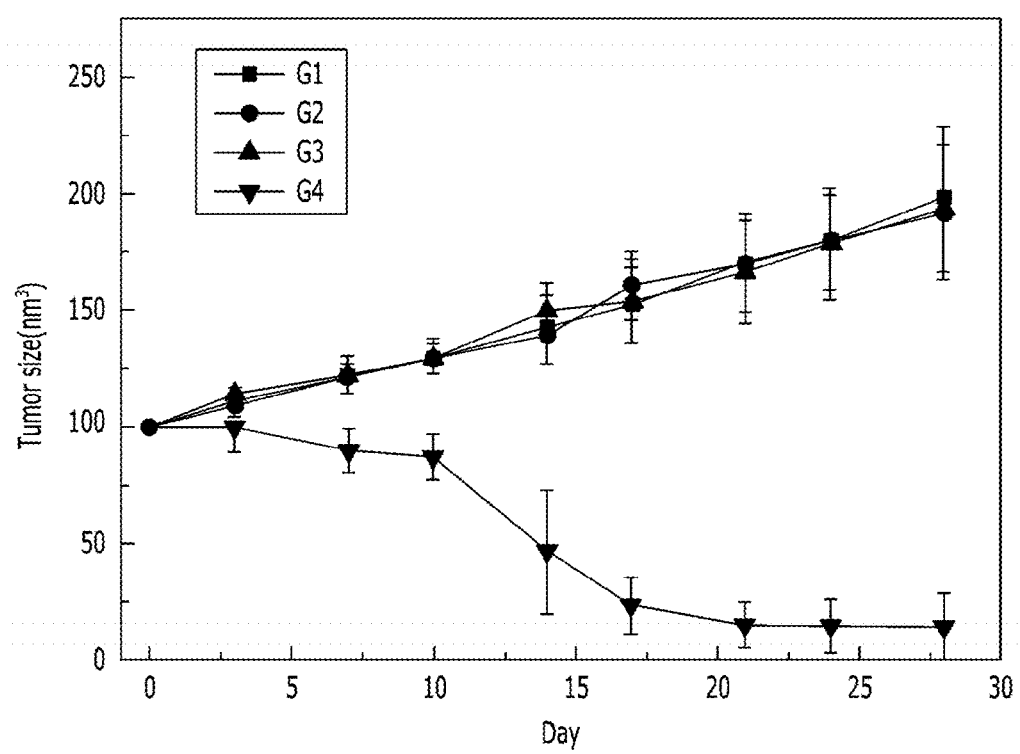
FIG. 6 is a graph showing the size of a cancer over time after performing an in vivo thermotherapy test using particles according to an embodiment of the present invention.

FIG. 6 shows that cell death by thermotherapy using the iron oxide magnetic particles according to the present invention effectively occurs in vivo as well. Panc-1 cells were transplanted into a Balb/c nude mouse, and then when the size of cancer tissues became 100 mm3, a composition including the iron oxide magnetic particles of the present invention (150 μl of an aqueous solution obtained by dispersing 3 mg of iron oxide magnetic particles doped with 6% CuI in deionized water) was subcutaneously administered. Thereafter, an alternating magnetic field generator (100 kHz, 80 G) was applied for 30 minutes to perform thermotherapy, and the volume of a cancer was observed for 28 days. As a result, the volume of the cancer was 93% smaller than that of an induced control group (G1), so that it was confirmed that the growth of the cancer was effectively suppressed.

TABLE 3

| Group | Gender | Number of animals (Head) | Administered substance | Alternating magnetic field Generating device Applied or not | Route for administration | Dosage (μL/head) |
| --- | --- | --- | --- | --- | --- | --- |
| G1 | F | 5 | — | N | — | — |
| G2 | F | 5 | ZTi Biosciences Experiment substance | N | Direct injection | Test substance: 150 |
| G3 | F | 5 | — | Y | — | — |
| G4 | F | 5 | ZTi Biosciences Experiment substance | Y | Direct injection | Test substance: 150 |

Example 6: Toxicity Test when Administered In Vivo

Table 4 shows blood biochemical and electrolyte values examined before and on Day 1, Day 7, Day 14, and Day 28 after administering 150 μl of the composition according to the present invention to a Balb/c nude mouse. There was no significant decrease and/or increase in numerical values. After an intravenous injection, hepatotoxicity indicators (ALP, ALT, and AST) were slightly increased, and as kidney toxicity indicators, Glucose decreased and Creatinine and K were increased, but returned to normal on Day 7 to Day 14.

TABLE 4

| Parameters | | Day | | | | |
|---|---|---|---|---|---|---|
| | | 0 | 1 | 7 | 14 | 28 |
| Albumin(g/dl) | Mean | 1.83 | 1.47 | 1.55 | 1.62 | 1.50 |
| | SD | 0.06 | 0.07 | 0.38 | 0.21 | 0.06 |
| ALP(U/L) | Mean | 521.23 | 278.19 | 315.89 | 464.99 | 370.19 |
| | SD | 40.3 | 39.2 | 65.1 | 100.1 | 27.4 |
| ALT(U/L) | Mean | 38.7 | 169.2 | 30.6 | 35.6 | 32.6 |
| | SD | 5.5 | 38.1 | 11.3 | 20.7 | 3.7 |
| AST(U/L) | Mean | 111.77 | 1376.52 | 89.23 | 81.57 | 78.32 |
| | SD | 21.8 | 150.6 | 19.1 | 38.9 | 6.2 |
| T. Bil(mg/dl) | Mean | 0.28 | 0.21 | 0.18 | 0.15 | 0.12 |
| | SD | 0.01 | 0.05 | 0.03 | 0.02 | 0.03 |
| BUN(mg/dl) | Mean | 42.30 | 168.32 | 52.01 | 40.30 | 39.10 |
| | SD | 5.42 | 28.19 | 30.22 | 5.20 | 2.88 |
| Ca(mg/dl) | Mean | 6.55 | 8.01 | 8.02 | 8.21 | 8.57 |
| | SD | 0.72 | 1.66 | 0.98 | 0.61 | 0.19 |
| Creatinine(mg/dl) | Mean | 0.33 | 1.225 | 0.319 | 0.487 | 0.29 |
| | SD | 0.01 | 0.24 | 0.19 | 0.07 | 0.08 |
| Glucose(mg/dl) | Mean | 200.19 | 107.75 | 169.35 | 207.22 | 309.44 |
| | SD | 20.7 | 38.5 | 59.2 | 37.2 | 45.8 |
| Na(mmol/L) | Mean | 150.12 | 132 | 138.1 | 140.3 | 143.11 |
| | SD | 3.5 | 3.9 | 3.0 | 2.7 | 2.5 |
| K(mmol/L) | Mean | 5.99 | 9.04 | 6.12 | 5.04 | 5.61 |
| | SD | 0.2 | 1.7 | 1.9 | 0.8 | 0.8 |
| Cl(mmol/L) | Mean | 110.7 | 102 | 98.2 | 99.3 | 105.8 |
| | SD | 0.7 | 3.2 | 2.1 | 3.3 | 2.3 |

Examples 7 to 19: Synthesis of Iron Oxide Magnetic Particles Including MXn (a) Synthesis of Iron-Oleic Acid or Iron-Oleylamine Composite In order to meet the ratios of Table 5 and Table 6 below, FeCl3·6H2O and sodium oleate (28 mmol) (Examples 7 to 11 and Examples 17 to 19) or oleylamine (28 mmol) (Examples 12 to 16) were mixed with 200 ml of hexane, 100 ml of ethanol, and 100 ml of deionized water, and reacted while being vigorously stirred at 110° C. for 6 hours. The reaction solution was cooled at room temperature, and then a transparent lower layer thereof was removed using a separatory funnel. 100 ml of water was mixed with a brown upper organic layer and shaken, and then a lower water layer was removed again. The above was repeated for three times. The remaining brown organic layer was transferred to a beaker and heated at 110° C. for 4 hours to allow hexane to evaporate.

(b) Synthesis of MXn-Doped Iron Oxide Magnetic Particles 4.5 g (5 mmol) of the iron-oleic acid composite prepared in (a) and 1.7 g (6 mmol) of oleic acid were mixed (Examples 7 to 11 and Examples 17 to 19) or 4.280 g (5 mmol) of the iron-oleylamine composite prepared in (a) and 1.6 g (6 mmol) of oleylamine were mixed (Examples 12 to 16). Thereafter, MXn of the types and contents of Tables 4 and 5 below were respectively mixed with 7 ml of 1-eicosene and 13 ml of dibenzyl ether. The mixture was placed in a round bottom flask, and gas and moisture were removed at 90° C. for about 30 minutes in a vacuum state. Nitrogen was injected thereto, and the temperature was raised to 200° C. Thereafter, the temperature of the mixture was raised to 310° C. at a rate of 3.3° C./min, and then the mixture was reacted for 60 minutes. The reaction solution was cooled, and then transferred to a 50 ml conical tube. 30 ml of ethanol and hexane were injected in a 1:1 ratio, followed by centrifugation to precipitate particles. The precipitated particles were washed with 10 ml of hexane and 5 ml of ethanol, and then an obtained precipitate was dispersed in toluene or hexane. Here, the dibenzyl ether is decomposed into benzyl aldehyde and toluene at a temperature of 150° C. or higher, and by radicals generated from the aldehyde, participates in crystal formation by helping the formation of a hydrogen bond between Iron oxo (—Fe—O—Fe—) and a heavy atom-halogen compound (MXn). The size of particles prepared thereby was about 6 to 7 nm.

TABLE 5

| Notes | Iron composite (Iron-oleic acid or iron oleylamine content g) | $MX_n$ type (Content g) | Weight ratio of $MX_n$ to iron composite (Input amount during manufacturing) | Weight ratio of $MX_n$ based on iron oxide (After material formation, analysis value: based on ICP) |
|---|---|---|---|---|
| Example 7 | 4.501 g (5 mmol) | CuI 0.045 g (0.236 mmol) | 0.010 | 0.009 |
| Example 8 | 4.501 g (5 mmol) | CuI 0.135 g (0.708 mmol) | 0.030 | 0.028 |
| Example 9 | 4.501 g (5 mmol) | CuI 0.270 g (1.416 mmol) | 0.060 | 0.057 |
| Example 10 | 4.501 g (5 mmol) | CuI 0.022 g (0.118 mmol) | 0.005 | 0.003 |
| Example 11 | 4.501 g (5 mmol) | CuI 0.450 g (2.360 mmol) | 0.100 | 0.091 |
| Example 12 | 4.280 g (5 mmol) | CuI 0.045 g (0.236 mmol) | 0.010 | 0.007 |
| Example 13 | 4.280 g (5 mmol) | CuI 0.135 g (0.708 mmol) | 0.030 | 0.029 |
| Example 14 | 4.280 g (5 mmol) | CuI 0.270 g (1.416 mmol) | 0.060 | 0.059 |
| Example 15 | 4.280 g (5 mmol) | CuI 0.022 g (0.118 mmol) | 0.005 | 0.004 |
| Example 16 | 4.280 g (5 mmol) | CuI 0.450 g (2.360 mmol) | 0.100 | 0.097 |

TABLE 6

| Notes | Iron composite (Iron-oleic acid content g) | MX$_n$ type (Content g) | Weight ratio of MX$_n$ to iron composite (Input amount during manufacturing) | Weight ratio of MX$_n$ based on iron oxide (After material formation, analysis value: based on ICP) |
|---|---|---|---|---|
| Example 17 | 4.501 g (5 mmol) | CuF 0.270 g (3.271 mmol) | 0.060 | 0.058 |
| Example 18 | 4.501 g (5 mmol) | CuCl 0.270 g (2.727 mmol) | 0.060 | 0.056 |
| Example 19 | 4.501 g (5 mmol) | CuBr 0.270 g (1.882 mmol) | 0.060 | 0.058 |

(C) Preparation of Iron Oxide Magnetic Particles Coated with Hydrophilic Ligand (Polyacrylic Acid)

2 g of polyacrilic acid and 40 ml of tetraethylene glycol were heated at 110° C., and then 150 mg of iron oxide magnetic particles of Examples 7 to 19 dispersed in 5 ml of hexane was injected thereto with a syringe. The mixture was stirred and reacted at 280° C. for 8 hours. The reaction solution was cooled, and then 20 ml HCl of 0.01 N was added thereto to collect iron oxide magnetic particles attracted to a magnet. After repeating the above twice, a precipitate was obtained using ethanol and was finally dispersed in water.

Experimental Example: Analysis of Temperature Change According to Weight Ratio of Iron Oxide and MXn Under External Alternating Magnetic Field The iron oxide magnetic particles prepared in each of Examples 7 to 19 were coated with polyacrylic acid, which is a hydrophilic ligand, and then the self-induced heating ability thereof was tested. The iron oxide magnetic particles of each of Examples 7 to 19 coated with polyacrylic acid were diluted to a concentration of 20 mg/ml in deionized water, and then an alternating magnetic field was applied thereto to measure the temperature change using a thermocouple (OSENSA, Canada). (Used alternating current frequency and magnetic field intensity: f=108.7 kHz, H=11.4 kA/m) The results are shown in Table 7 below.

A system for heating by inducing an alternating magnetic field consists of four main subsystems; (a) A variable frequency and amplitude sine wave function generator (20 MHz Vp-p, TG2000, Aim TTi, USA)), (b) A power amplifier (1200 Watt DC Power Supply, QPX1200SP, Aim TTi, USA), (c) An induction coil (rotation number: 17, diameter: 50 mm, height: 180 mm) and a magnetic field generator (Magnetherm RC, nanoTherics, UK), and (d) A temperature change thermocouple (OSENSA, Canada).

TABLE 7

| | Temperature reached per unit time (Standard: 1 minute) Start measuring at 25° C. |
|---|---|
| Example 7 | 41° C. |
| Example 8 | 64° C. |
| Example 9 | 86° C. |
| Example 10 | 27° C. |
| Example 11 | 82° C. |
| Example 12 | 31° C. |
| Example 13 | 58° C. |
| Example 14 | 79° C. |

TABLE 7-continued

| | Temperature reached per unit time (Standard: 1 minute) Start measuring at 25° C. |
|---|---|
| Example 15 | 28° C. |
| Example 16 | 77° C. |
| Example 17 | 71° C. |
| Example 18 | 55° C. |
| Example 19 | 57° C. |

Experimental Example: Measurement of Specific Loss Power (SLP)

The calorific value of iron oxide magnetic particles varies depending on the physical and chemical properties, and the intensity and frequency of an external alternating magnetic field, most research results represent the heating ability of particles as SLP and ILP. SLP is electromagnetic force lost per mass unit and is represented by W (watts) per kg. Since the conditions of f (frequency) and H (magnetic field intensity) may be different for each experiment, it is possible to compare thermotherapy effects between particles by converting an SLP value to an ILP value using the equation [ILP=SLP/(fH$^2$)].

SLP was measured by using an alternating magnetic field generator (Magnetherm RC, Nanotherics) of a series resonance circuit controlled by a pickup coil and an oscilloscope. The measurement was performed under the thermal insulation condition of f=108.7 kHz and H=11.4 kA/m, and the temperature was measured using an optical fiber IR probe.

SLP was measured by adjusting the concentration of the iron oxide magnetic particles prepared in each of Examples 7 to 19 to 20 mg/ml. The results are shown in Table 8 below.

TABLE 8

| | ILP value |
|---|---|
| Example 7 | 2.57 |
| Example 8 | 6.26 |
| Example 9 | 10.60 |
| Example 10 | 0.32 |
| Example 11 | 9.15 |
| Example 12 | 0.96 |
| Example 13 | 5.30 |
| Example 14 | 9.17 |
| Example 15 | 0.48 |
| Example 16 | 8.35 |
| Example 17 | 7.39 |
| Example 18 | 5.81 |
| Example 19 | 5.34 |

Experimental Example: Experiment to Confirm Cancer Treatment Effect In Vivo

It was confirmed that cell death by thermotherapy using the iron oxide magnetic particles of each of Examples 7 to 19 and Control Groups of the present invention effectively occurred in vivo as well. Panc-1 cells were transplanted into a Balb/c nude mouse, and then when the size of cancer tissues became about 100 mm$^3$, 150 μl of an aqueous solution obtained by dispersing a composition including the iron oxide magnetic particles of each of Examples 7 to 19 and Control Group 1 was subcutaneously administered. Thereafter, an alternating magnetic field generator (100 kHz, 80 G) was applied for 30 minutes to perform thermotherapy, and the volume of a cancer was observed for 28 days.

The results are shown in Table 9 below.

TABLE 9

| Notes | Final tumor size after treatment (mm$^3$) | | | | |
|---|---|---|---|---|---|
| (Measurement week) | (Week 0) | (Week 1) | (Week 2) | (Week 3) | (Week 4) |
| Example 7 | 101 | 88 | 51 | 48 | 41 |
| Example 8 | 97 | 70 | 45 | 39 | 31 |
| Example 9 | 98 | 65 | 21 | 18 | 15 |
| Example 10 | 100 | 151 | 280 | 430 | 620 |
| Example 11 | 97 | 71 | 53 | 42 | 39 |
| Example 12 | 99 | 149 | 270 | 421 | 610 |
| Example 13 | 98 | 79 | 48 | 34 | 29 |
| Example 14 | 98 | 71 | 35 | 27 | 22 |
| Example 15 | 103 | 161 | 290 | 464 | 682 |
| Example 16 | 96 | 78 | 63 | 42 | 35 |
| Example 17 | 98 | 76 | 41 | 33 | 29 |
| Example 18 | 99 | 78 | 49 | 32 | 26 |
| Example 19 | 101 | 74 | 51 | 31 | 24 |
| Control Group 1 (Iron oxide Fe$_3$O$_4$) | 97 | 171 | 290 | 440 | 730 |

Experimental Example: Measurement of Radiation Absorption Coefficient (HU)

The radiation (X-ray) absorption coefficient (HU) was measured using the iron oxide magnetic particles prepared in each of Examples and Control Groups, and the results are shown in Table 10 below. At this time, the measurement device was Bruker Co., Ltd.'s Skyscan 1172 Micro CT, and the radiation absorption coefficient (HU) was calculated as follows.

CT Hounsfield Unit (HU, X-ray absorption coefficient)

$$HU = 1000 \times \frac{\mu - \mu_{water}}{\mu_{water} - \mu_{air}}$$

(μ (Linear attenuation coefficient): Relative linear attenuation coefficient)

TABLE 10

| Notes | Radiation absorption coefficient per unit weight (based on 1 mg) (HU) |
|---|---|
| Example 7 | 61 |
| Example 8 | 88 |
| Example 9 | 97 |
| Example 10 | 10 |
| Example 11 | 97 |
| Example 12 | 68 |
| Example 13 | 84 |
| Example 14 | 95 |
| Example 15 | 11 |
| Example 16 | 94 |
| Example 17 | 74 |
| Example 18 | 73 |
| Example 19 | 78 |
| Control Group 4 (Iron oxide Fe$_3$O$_4$, see reference: Sci Rep., 8, 12706 (2018)) | About 10 |

Experimental Example: Thermogravimetric (TGA) Analysis of Iron Oxide Magnetic Particles In order to see the thermal stability of the iron oxide magnetic particles of the present invention (purpose: to confirm how stably halogen elements are bonded to iron oxide magnetic particles), thermogravometric analysis (TGA) was performed using Scinco Co., Ltd.'s S-1000. Specifically, the particles of each of Control Groups 1 to 3 and Examples 7 to 19 were compared by measuring the weight thereof up to 200° C. at a ratio of 20/min under nitrogen using a thermogravimetric analysis (TGA) device. The results are shown in Table 11.

TABLE 11

| Notes | Weight reduction ratio (%) |
|---|---|
| Example 7 | 4 |
| Example 8 | 4 |
| Example 9 | 3 |
| Example 10 | 6 |
| Example 11 | 5 |
| Example 12 | 5 |
| Example 13 | 4 |
| Example 14 | 3 |
| Example 15 | 7 |
| Example 16 | 4.7 |
| Example 17 | 7 |
| Example 18 | 6 |
| Example 19 | 6 |
| Control Group 1 (Iron oxide Fe$_3$O$_4$) | 15 |
| Control Group 2 (Iron oxide - KI 6 wt % doping) | 17 |
| Control Group 3 (Iron oxide - MgI$_2$ 6 wt % doping) | 13 |

As described above, iron oxide magnetic particles of the present invention may have high reactivity to a stimulus introduced from the outside, such as radiation, magnetic fields, and radio waves.

In addition, a contrast agent including the iron oxide magnetic particles may be applied to various imaging diagnosis devices, and sufficient images may be obtained by administering a small dose.

Furthermore, due to the bond formed between an iron oxide and MXn, the iron oxide magnetic particles have a highly stable structure. Therefore, there is no risk of side effects which may be caused by the component of each iron oxide magnetic particle, and toxicity is low, so that the iron oxide magnetic particles may be safely applied to a human body.

What is the claimed is:

1. Iron oxide magnetic particles comprising an iron oxide and $MX_n$,
    wherein the $MX_n$ comprises one or more selected from the group consisting of CuBr and CuI, and a weight ratio of the iron oxide to the $MX_n$ is 1:0.005 to 1:0.08, and wherein at least a portion of the surface of the iron oxide magnetic particles is further coated with a hydrophilic ligand and, wherein the hydrophilic ligand comprises one or more selected from the group consisting of polyethylene glycol, polyethylene amine, polyethylene imine, polyacrylic acid, polymaleic anhydride, polyvinyl alcohol, polyvinylpyrrolidone, polyvinyl amine, polyacrylamide, phosphate-polyethylene glycol, polybutylene terephthalate, polylactic acid, polytrimethylene carbonate, polydioxanone, polypropylene oxide, polyhydroxyethyl methacrylate, starch, dextran derivative, sulfonic acid, amino acid, sulfonic acid peptide, silica, and polypeptide.

2. The iron oxide magnetic particles of claim 1, wherein the $X_n$ is I.

3. The iron oxide magnetic particles of claim 1, wherein the X includes a radioactive isotope of X or a mixture of radioactive isotopes of X.

4. The iron oxide magnetic particles of claim 1, wherein the iron oxide is derived from a composite of iron and one or more compounds selected from the group consisting of an aliphatic carboxylate having 4 to 25 carbon atoms and an amine compound.

5. The iron oxide magnetic particles of claim 1, wherein the iron oxide comprises one or more selected from the group consisting of $Fe_{13}O_{19}$, $Fe_3O_4$ (magnetite), $\gamma\text{-}Fe_2O_3$ (maghemite), and $\alpha\text{-}Fe_2O_3$ (hematite), $\beta\text{-}Fe_2O_3$ (beta phase), $\varepsilon\text{-}Fe_2O_3$ (epsilon phase), FeO (Wustite), $FeO_2$ (Iron Dioxide), $Fe_4O_5$, $Fe_5O_6$, $Fe_5O_7$, and $Fe_{25}O_{32}$.

* * * * *